US009365692B2

(12) United States Patent
Schofalvi et al.

(10) Patent No.: US 9,365,692 B2
(45) **Date of Patent: *Jun. 14, 2016**

(54) IMPACT ABSORBING FOAM

(71) Applicant: Provee Technologies, LLC, Solon, OH (US)

(72) Inventors: Karl-Heinz Schofalvi, Solon, OH (US); Ji Seung Kim, Jersey City, NJ (US); Christopher James Durning, New York, NY (US)

(73) Assignee: Provee Technologies, LLC, Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/510,281

(22) Filed: Oct. 9, 2014

(65) Prior Publication Data

US 2015/0020573 A1 Jan. 22, 2015

Related U.S. Application Data

(63) Continuation of application No. 13/569,202, filed on Aug. 8, 2012, now Pat. No. 8,883,869.

(51) Int. Cl.

| | |
|---|---|
| ***C08J 9/00*** | (2006.01) |
| ***C08K 7/24*** | (2006.01) |
| ***C08K 3/10*** | (2006.01) |
| ***C08G 18/48*** | (2006.01) |
| ***C08G 18/76*** | (2006.01) |
| ***C08G 18/18*** | (2006.01) |
| ***B29C 67/20*** | (2006.01) |
| ***C08G 18/32*** | (2006.01) |
| ***C08J 9/12*** | (2006.01) |
| ***G01K 13/00*** | (2006.01) |
| ***G01N 21/25*** | (2006.01) |
| ***G01N 33/00*** | (2006.01) |
| *C08G 101/00* | (2006.01) |
| *B29K 101/12* | (2006.01) |
| *B29K 509/02* | (2006.01) |

(52) U.S. Cl.

CPC ............... *C08J 9/0066* (2013.01); *B29C 67/20* (2013.01); *C08G 18/1808* (2013.01); *C08G 18/3206* (2013.01); *C08G 18/4825* (2013.01); *C08G 18/4829* (2013.01); *C08G 18/7614* (2013.01); *C08G 18/7621* (2013.01); *C08J 9/122* (2013.01); *C08K 3/10* (2013.01); *C08K 7/24* (2013.01); *G01K 13/00* (2013.01); *G01N 21/25* (2013.01); *G01N 33/0004* (2013.01); *B29K 2101/12* (2013.01); *B29K 2509/02* (2013.01); *C08G 2101/00* (2013.01); *C08G 2101/0008* (2013.01); *C08G 2101/0083* (2013.01); *C08J 2375/08* (2013.01); *C08K 2201/003* (2013.01)

(58) Field of Classification Search

USPC ................. 521/76, 91, 92, 159; 523/218, 219

See application file for complete search history.

(56) References Cited

U.S. PATENT DOCUMENTS

| | | | | |
|---|---|---|---|---|
| 3,398,106 | A | 8/1968 | Hostettler et al. | |
| 4,271,537 | A * | 6/1981 | Bowlus et al. | 2/424 |
| 6,166,109 | A | 12/2000 | Spitler et al. | |
| 6,833,390 | B2 | 12/2004 | Haider et al. | |

FOREIGN PATENT DOCUMENTS

| | | |
|---|---|---|
| WO | 95/19943 | 7/1995 |

OTHER PUBLICATIONS

Data Sheet for Qcel 300, 2013.
Data Sheet for Scotchlite from 3M, 2003.
Data Sheet for Trimethyolpropane, Chemicalland21, 2013.

* cited by examiner

*Primary Examiner* — Kara Boyle

(74) *Attorney, Agent, or Firm* — Renner, Otto, Boisselle & Sklar, LLP

(57) ABSTRACT

This invention relates to impact absorbing foams. These foams comprise a polymeric foam and ceramic particulates dispersing the foam. These foams have numerous uses, including, for example, as interior pads for football helmets, and the like, for reducing head injuries.

36 Claims, No Drawings

IMPACT ABSORBING FOAM

TECHNICAL FIELD

This invention relates to impact absorbing foams and, more particularly, to impact absorbing foams comprising a polymeric foam containing ceramic particulates.

BACKGROUND

Impact absorbing polymeric foams are typically designed to absorb at impact about 15% of the energy resulting from the impact.

SUMMARY

This invention relates to impact absorbing foams which may absorb at impact at least about 20%, or at least about 30%, or at least about 40%, or at least about 50%, or at least about 60%, or at least about 75%, or at least about 85% of the energy resulting from such impact. These impact absorbing foams may have numerous uses including, for example, as interior pads for football helmets. These foams may absorb energy resulting from impact against the helmet during play with the result being a reduction in head injuries, including concussions, and the like.

This invention relates to an impact absorbing foam comprising: a polymeric foam; and ceramic particulates dispersed in the polymeric foam; wherein the ceramic particulates have an average particle size in the range from about 1 to about 400 microns, or from about 30 to about 300 microns, or from about 50 to about 150 microns, or about 100 microns; and a crushing strength in the range from about 100 to about 2,000,000 pounds per square inch (psi), or in the range from about 100 to about 1,000,000 psi, or in the range from about 100 to about 500,000 psi, or in the range from about 100 to about 250,000 psi, or in the range from about 250 to about 100,000 psi, or in the range from about 3000 to about 60,000 psi. The average distance between the ceramic particulates in the foam may be in the range from about 100 to about 2000 microns, or from about 300 to about 1000 microns, or from about 500 to about 700 microns, or about 600 microns.

DETAILED DESCRIPTION

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "ceramic" is used herein to refer to an inorganic solid material. The ceramic particulates may comprise oxides (e.g., alumina, ceria, zirconia), non-oxides (e.g., carbide, boride, nitride, silicide), or mixtures of two or more thereof. The ceramic particulates may be in an "as mined" form, or may be in a treated or processed form, for example, by sintering, calcining, and the like.

The invention relates to an impact absorbing foam comprising a polymeric foam and ceramic particulates dispersed in the polymeric foam. The ceramic particulates may comprise one or more energy absorbing ceramic fracture materials. The invention contemplates various morphologies, chemical compositions, concentrations, spatial distributions, fracture energies, sintering conditions, shape formation processes, surface coupling agents and particle size distributions for the ceramic particulates. The properties of the foam may be controlled by the selection of ingredients and the process used to polymerize the ingredients. The processes for making these foams may include in-situ ceramic particulate addition during polymerization and foam creation. The invention contemplates various production processes for combining the polymeric foam and ceramic particulates. The invention provides for various degrees of freedom for tailoring final properties for the foam to maximize performance as an energy absorbing material for use in a broad range of applications from protective helmets to automotive crush zones, and the like.

The foam may comprise a continuous polymeric phase and a discontinuous phase comprising gas bubbles and/or void spaces dispersed in the polymeric phase. The polymeric phase may comprise a polymer, the polymer comprising polyurethane, polystyrene, polyvinyl chloride, polybutadiene, halogenated butyl rubber, styrene-butadiene rubber, polyacrylic rubber, butyl rubber, ethylene-propylene rubber, neoprene rubber, hypalon rubber, polysulfide elastomer, polysilicone, fluorocarbon rubber, polyhexafluoropropylene, polytetrafluoroethylene, polypropylene, polychlorotrifluoroethylene, polymethylvinyl ether, or a mixture of two or more thereof.

The polymer may comprise a thermoset polymer. Gelation is a typical characteristic of thermoset polymers and a phenomenon that may take place during thermosetting polymer cure reactions. It corresponds to the incipient formation of a network. Gelation may occur at a well-defined stage in the course of the cure reaction and depends on the stoichiometry, functionality, and reactivity of reactants, and temperature. This phenomenon may occur for conversions between about 55 and about 80% (fractional conversion is 0.55-0.80). Prior to gelation, the polymer may be dissolved in appropriate solvents. After the gel point, however, the network may not dissolve but swell in certain solvents. Soluble small and branched molecules may be present. The curing polymer may contain sol as well as gel fractions.

The polyurethanes may be referred to as addition polymers formed by the reaction of di- or poly-isocyanates with a polyol. The molecular structures may vary from rigid cross-linked polymers to linear, highly extensible elastomers. The curing of the polyurethane may involve the formation of a three-dimensional network through reactions among polyfunctional groups. The curing process may start from the formation and linear growth of a chain. The chain may then branch and cross-link. As the curing proceeds, the molecular weight may increase, and a plurality of chains may be linked together to form a network. Polyurethanes based on methylene diphenyl diisocyanate (MDI) and toluene diisocyanate (TDI) may be particularly useful because of their advantageous mechanical properties. The polyol may have a molecular weight in the range from about 100 to about 125,000, or from about 100 to about 50,000, or about 500 to about 30,000, or from about 100 to about 10,000, or from about 2000 to about 4000, or about 3000. The polyol may have a hydroxyl number in the range from about 10 to 200, an average functionality in the range from 1 to about 12, and a density in the range from about 0.9 to about 1.3 g/mol.

The polymeric phase may be derived from a polyurethane pre-polymer. The polyurethane pre-polymer may comprise a toluene diisocyanate and/or methylene diphenyl diisocyante terminated pre-polymer. The polyurethane pre-polymer may have an average molecular weight in the range from about 100 to about 125,000, or from about 100 to about 50,000, or from about 500 to about 10,000. The polyurethane pre-polymer may have an average functionality in the range from about 1 to about 10, and a density in the range from about 0.9 to about 1.3 g/cc.

The gas bubbles and/or void spaces may be derived from one or more blowing agents. These may include water, chlorofluorocarbons, hydrochlorofluorocarbons, hydrocarbons (e.g., pentane, isopentane, cyclopentane), liquid $CO_2$, hydrazine, sodium bicarbonate, and the like, or a mixture of two or more thereof. The water may be taken from any source and may comprise deionized water (DI water) and/or water that is purified via osmosis or distillation.

When the foam comprises a polyurethane foam, the gas bubbles and/or void spaces may be derived from the reaction of water with an isocyante. For example, in the preparation of a polyurethane foam, an excess of isocyanate over that needed to react with the polyol may be used to react with the water. For example, an excess of about 5% by weight isocyanate may be used. The resulting gas bubbles may comprise carbon dioxide.

The foam may comprise a polyurethane foam derived from a polyurethane pre-polymer, a plasticizer, a surfactant, one or more catalysts, an isocyanate, and water. The plasticizer may comprise a mono-, di- and/or tri-alkyl phthalate and/or phosphate. The surfactant may comprise a polysiloxane, such as polydimethylsiloxane. The catalyst may comprise dibutyltin dilaureate, stannous octoate, and/or tetramethyl-1,6-hexadiamine.

The gas bubbles and/or void spaces may provide the foam with a volumetric expansion in the range from about 50% to about 400%, or from about 100% to about 375%, or from about 120% to about 360%, or from about 150% to about 250%, or about 200%.

The ceramic particulate may comprise a frangible material, which may be dispersed in the polymer foam matrix to provide an energy absorbing effect, when impact energy is delivered to the foam. The ceramic particulates may comprise aluminum, zirconium, silicon, magnesium, calcium, boron, silicon, carbide, oxides thereof, or mixtures of two or more thereof. The ceramic particulates may be in the form of platelets, flakes, hollow spheres, solid spheres, rods, cones, hollow irregular shaped particulates, solid irregular shaped particulates, coated particulates, laminar particulates, laminated particulates, composite particulates, or a mixture of two or more thereof.

The ceramic particulates may comprise hollow alumino-silicate spheres, silicon carbide flakes, natural mica flakes, chemically modified mica flakes, aluminum diboride flakes, boron nitride platelets, sodium silicate coated ceramic spheres, potassium ion modified mica flakes, alumina flakes, hollow alumina spheres, zirconia particulates, hollow zirconia spheres, sol-gel or aerosol produced silica, or a mixture of two or more thereof.

The ceramic particulates may be coated with one or more layers of sodium silicate, silica, alumina, alumino-silica, zirconia, titania, calcia, magnesia, or mixtures of two or more thereof. For example, the ceramic particulates may comprise a ceramic fracture material which initially comprises a spray dried and sintered alumino-silicate hollow spheres which are then coated with sodium silicate. The weight ratio of silica to alumina may be about 3:1. The sodium silicate coating may be provided using a sodium silicate solution such as Ludox AS-40, which is available from DuPont.

The ceramic particulates may comprise hollow particulates (e.g., hollow microspheres) containing an inert gas. The inert gas may comprise nitrogen, argon, helium, and the like, or a mixture of two or more thereof.

The concentration of the ceramic particulates in the polymeric foam may be in the range from about 10 to about 60% by volume, or from about 20 to about 50% by volume, or from about 30% to about 40% by volume, based on the combined volume of the polymeric foam and the ceramic particulates.

The foam may be provided in the form of a padding material, a component of a shoe, a prosthetic device, a component of a protective helmet, a padding to protect mechanical or electrical equipment, and/or a protective material for the interior of a vehicle. The foam may be used as an interior pad for a football helmet.

The ceramic particulates may have a crushing strength in the range from 100 to about 2,000,000 psi, or from about 100 to about 1,000,000 psi, or from about 100 to about 500,000 psi, or from about 100 to about 250,000 psi, or from about 250 to about 100,000 psi, or from about 3000 to about 60,000 psi.

The crushing strength may be determined using the test method described in ASTM C773.

The foam may be capable of absorbing on impact at least about 20%, or at least about 30%, or at least about 40%, or at least about 50%, or at least about 60%, or at least about 75%, or at least about 85% of the energy resulting from such impact. The energy absorbed may be determined using the test described in ASTM D4168 95 (2008) e 1.

The foam may have a Young's modulus in the range from about 0.3 to about 75 GPa, or from about 0.3 to about 5 GPa, or from about 0.5 to about 2 GPa, or from about 5 to about 75 GPa, or from about 5 to about 15 GPa. This modulus may be determined using the test method described in ASTM D638-10.

The foam may have a tensile strength in the range from about 0.001 to about 100 mega Newtons per square meter ($MN/m^2$), or from about 0.1 to about 20 $MN/m^2$, or from about 0.5 to about 10 $MN/m^2$. Tensile strength may be determined using the test method described in ASTM D3574-11.

In use, an impacting force may be applied against the foam which may result in the crushing of at least some of the ceramic particulates in the foam. The crushing of the ceramic particulates cushions the blow applied against the foam and thereby protects articles or objects in contact with the foam from the blow. For example, the foam may be used as an interior pad for a football helmet. The foam may absorb energy resulting from impact against the helmet during play with the result being a reduction in head injuries, including concussions, and the like. The foam may absorb at impact at least about 20%, or at least about 30%, or at least about 40%, or at least about 50%, or at least about 60%, or at least about 75%, or at least about 85% of the energy resulting from such impact.

As indicated above, the ceramic particulates may comprise hollow particulates that may contain an inert gas. An impacting force applied against the foam may generate heat within the foam and crush at least some of the hollow particulates. The crushing of the hollow particulates may cause a release of inert gas within the foam. The release of inert gas within the foam may reduce at least some of the heat generated within the foam by the impacting force applied against the foam. The release of the inert gas may cool the heated foam. A heat sensor may be used to equate the amount of heat released to the amount of ceramic particulates crushed. A gas sensor may be used to equate the amount of inert gas released to the amount of ceramic particulates crushed. An indicating device may be used to measure the amount of ceramic particulates crushed. The indicating device may comprise a radio frequency identification (RFID) chip communicating with a sensor to monitor the force applied against the foam. The indicating device may comprise a colorimetric indicator that changes color indicating the amount of ceramic particulates that have been crushed.

The mechanical properties of the polymeric foam may be altered when the ceramic particulates are loaded into the polymeric matrix. In general, the polymeric foam may become stiffer and less elastomeric when the loading level of the ceramic particulates is in the range from about 25 to about 50% by volume.

The mechanical properties of the polymeric foam may depend on the size, distribution and nature (closed or open) of the gas bubbles or void spaces (known as "cells"). The foam may comprise a closed or open cell structure with an average cell diameter in the range from about 0.05 mm to about 1 mm in diameter, or in the range from about 0.1 to about 0.3 mm, or about 0.2 mm. The cell design may comprise a mixture of open and closed cells.

In the examples provided below a polyether polyol and a polyurethane pre-polymer are used. The polyether polyol is Voranol 3136, which is available from Dow. The polyurethane pre-polymer is a toluene 2,4-diisocyanate terminated polypropylene glycol (which may be referred to as PPG, 2,4-TDI terminated).

Voranol 3136 has the following properties:

Density: 1.0164 g/ml

Average functionality: 3

Average molecular weight (MW): 3100 g/mol

Hydroxyl number: 56

MW per OH functional group: 1033 g/mol OH

Molar volume per OH functional group: 1.0163 ml/OH group

The PPG, 2,4-TDI terminated polyurethane pre-polymer has the following properties:

Density: 1.05 g/ml

Functionality: 2

Average MW: 2300 g/mol

MW per CNO functional group: 1150 g/mol CNO

Molar volume per CNO functional group: 1.095 ml/CNO group

For 1 ml of the Voranol 3136 polyether polyol, 1.077 ml of PPG, 2,4-TDI terminated polyurethane pre-polymer may be used based on 1:1 equivalence ratio. However, foams may be prepared using a slight excess of isocyanate; e.g., 105% (or 5% excess) of theoretical equivalence. The isocyamate excess may be reacted with water to product $CO_2$ bubbles within the polymeric phase, and thereby provide the desired foam structure. Thus, for 1 ml of the Voranol 3136 polyether polyol, 1.13 ml of PPG, 2,4-TDI terminated polyurethane pre-polymer is used.

However, due to the fact that the CNO group can react with the OH group in deionized water as well as with the amine group of the diamine catalyst, the actual volume of the prepolymer input may be increased. For each 1 ml of deionized water and diamine catalyst added, the additional prepolymer input for stoichiometric balance may be 121.6 ml and 10.24 ml, respectively.

For 100 parts by weight (pbw) of the Voranol 3136 polyether polyol, the following ingredients are used:

20 pbw of plasticizer 3 pbw of surfactant 6 pbw of dibutyl tin dilaurate catalyst 3 pbw of tetramethyl-1,6-hexadiamine catalyst 0.3 to 5.0 pbw deionized water This is shown in the following formulation:

| | Name | Volume (ml) | Density (g/ml) | Note | Pbw per 100 pbw of pre-polymer |
|---|---|---|---|---|---|
| Polyurethane Pre-polymer (A-side reactant) | PPG, 2,4-TDI terminated | 35.0 | 1.013 | 5% excess | |
| Polyol Resin Mixture (B-side mixture) | Voranol 3136 | 30.0 | 1.016 | polyol | |
| | Tritolyl phosphate | 5.3 | 1.143 | plasticizer | 0.2 |
| | Dimethyl polysiloxane | 0.9 | 0.98 | surfactant | 0.03 |
| | Dibutyltin dilaurate | 1.7 | 1.066 | catalyst | 0.06 |
| | Tetramethyl-1,6-hexadiamine | 1.1 | 0.806 | catalyst | 0.03 |

The following synthesis procedure is used:

1. Mix and agitate all components of the polyol resin mixture (B-side mixture) at 70° C. for 1.5 hours
2. Cool the polyol resin mixture to 40° C.
3. Preheat the polyurethane pre-polymer (A-side reactant) to 55° C.
4. Mix the polyurethane pre-polymer and polyol resin mixture in a Teflon beaker and rapidly agitate.
5. Leave the mixture to foam/harden for at least 10 minutes.
6. Demold the polyurethane foam, and cure the foam inside a laminar flow hood for 24 hours.

Notes:

1. The polymer forming or gelation reaction (reaction of isocyanate-polyol resulting in formation of urethane linkages) between the isocyanate and polyol is promoted by the dibutyl tin diluarate catalyst. This catalyst is believed to act as a Lewis acid and to function by interacting with basic sites in the isocyanate and polyol compounds.
2. The tetramethyl-1,6-diamine catalyst is believed to promote formation of isocyanate-water linkages.

EXAMPLE 1

An elastomeric polyurethane is prepared as follows:

In a 250 ml graduated beaker, 30 ml of Voranol 3136 are transferred using a 50 ml glass syringe. Subsequently, 5.3 ml of tritolyl phosphate (plasticizer), 0.9 ml of polydimethylsiloxane (surfactant), 1.7 ml of dibutyltin dilaurate (catalyst), and 1.1 ml of tetramethyl-1,6-hexadiamine (catalyst) are added using a 1 ml plastic pipette. This mixture, which may be referred to as a B-side mixture, is pre-heated at 70° C., while being stirred with magnetic stirring bar for 90 minutes. The magnetic stirring bar is then removed.

40 ml of PPG, 2,4-TDI terminated pre-polymer, which may be referred to as an A-side reactant, is pre-heated to 55° C. in a 150 ml polypropylene beaker for 12 minutes.

A 1000 ml Teflon PFA beaker is placed on a hot plate. The pre-heated B-side mixture is transferred into the beaker. The pre-heated A-side reactant is subsequently transferred into the beaker. The combined A-side reactant and B-side mixture are mixed for 3 minutes at a temperature of 55° C. using a metal spatula to form a polyurethane elastomer. The elastomer is heated at a temperature of 55° C. for 10 minutes, and then cured at room temperature for 24 hours.

EXAMPLES 2-6

A water-blown polyurethane foam is prepared as follows:

In a 250 ml graduated beaker, 30 ml of Voranol 3136 are transferred using a 50 ml glass syringe. Subsequently, 5.3 ml of tritolyl phosphate (plasticizer), 0.9 to 1.5 ml of dimethylpolysiloxane (surfactant), 1.7 ml of dibutyltin dilaurate (catalyst), and 1.1 ml of tetramethyl-1,6-hexadiamine (catalyst) are added using a 1 ml plastic pipette. This mixture may be referred to as a B-side mixture. The B-side mixture is pre-heated at 70° C., while being stirred with magnetic stirring bar, for 90 minutes. Deionized water (0.08 to 0.5 ml) is added to the mixture 3 minutes before the B-side mixture pre-heating is completed. The magnetic stirring bar is then removed.

40 to 85 ml of PPG, 2,4-TDI terminated pre-polymer, which may be referred to as an A-side reactant, is pre-heated at 50° C. in a 100 ml polypropylene beaker for 20 to 30 minutes.

Into a 600 ml polypropylene beaker, the pre-heated B-side mixture is transferred, and the pre-heated A-side reactant is subsequently transferred. The beaker is placed on a hot plate. The reactants are mixed for 3 minutes at a temperature of 55° C., heated for 10-60 minutes at 55° C., and then cured at room temperature for 24 hours to provide a polyurethane foam. The expansion of the foam is 200% of the original mixed volume of the components used to make the foam. The amounts of reactants and the post-mixing heating time for each example are shown in Table A.

TABLE A

| Example | Polydimethy siloxane | DI Water (ml) | Prepolymer (ml) | Heating Time (minutes) |
|---|---|---|---|---|
| 2 | 0.9 | 0.08 | 40 | 60 |
| 3 | 0.9 | 0.08 | 58 | 10 |
| 4 | 0.9 | 0.23 | 78 | 10 |
| 5 | 0.9 | 0.12 | 58 | 10 |
| 6 | 1.5 | 0.50 | 85 | 20 |

EXAMPLES 7-16

A water-blown polyurethane foam containing ceramic particulates dispersed in the foam is prepared as follows:

In a 250 ml graduated beaker, 30 ml of Voranol 3136 are transferred using a 50 ml glass syringe. Subsequently, 5.3 ml of tritolyl phosphate (plasticizer), 0.9 to 1.5 ml of dimethyl polysiloxane (surfactant), 1.7 ml of dibutyltin dilaurate (catalyst), and 1.1 ml of tetramethyl 1,6 hexadiamine (catalyst) are added using a 1 ml plastic pipette. This mixture may be referred to as a B-side mixture. The B-side mixture is preheated at 70° C., while being stirred with magnetic stirring bar, for 90 minutes. At the start of the pre-heating, 4.9 to 50 ml of INSULADD (a blend of hollow ceramic spheres having an average particle size of 100 microns available from Insuladd Queensland) are added to the B-side mixture with stirring. Deionized water (0.09 to 0.05 ml) is added to the mixture 3 minutes before the B-side mixture pre-heating is completed. At the end of 90 minutes of heating, the magnetic stirring bar is removed.

PPG, 2,4-TDI terminated pre-polymer, which may be referred to as an A-side reactant, is pre-heated to 50° C. in a 100 ml polypropylene beaker for 20 to 30 minutes.

A 600 ml polypropylene beaker is placed on a hot plate. The pre-heated B-side mixture is transferred into the beaker, and the pre-heated A-side reactant is subsequently transferred. The combined reactants are heated at 55° C. and mixed for 3 minutes using a metal spatula to form a polyurethane mixture. The polyurethane mixture is then heated at 55° C. for 20 minutes, and then cured at room temperature for 24 hours to provide a polyurethane foam. The expansion of the foam is 200% of the original volume of the components used to make the foam. The amounts of reactants for each example are shown in Table B.

TABLE B

| Example | Poly-dimethyl siloxane (ml) | DI Water (ml) | Pre-polymer (ml) | INSULADD (ml) | INSULADD (pbv of A + B side)* |
|---|---|---|---|---|---|
| 7 | 0.9 | 0.09 | 57.9 | 24.3 | 25 |
| 8 | 0.9 | 0.09 | 57.9 | 19.4 | 20 |
| 9 | 0.9 | 0.09 | 57.9 | 14.6 | 15 |
| 10 | 0.9 | 0.09 | 57.9 | 9.7 | 10 |
| 11 | 0.9 | 0.09 | 57.9 | 4.9 | 5 |
| 12 | 1.5 | 0.30 | 75 | 28.6 | 25 |
| 13 | 1.5 | 0.38 | 75 | 23.0 | 20 |

TABLE B-continued

| Example | Poly-dimethyl siloxane (ml) | DI Water (ml) | Pre-polymer (ml) | INSULADD (ml) | INSULADD (pbv of A + B side)* |
|---|---|---|---|---|---|
| 14 | 1.5 | 0.50 | 85 | 18.8 | 15 |
| 15 | 1.5 | 0.50 | 85 | 37.5 | 30 |
| 16 | 1.5 | 0.50 | 85 | 50.0 | 40 |

*PBV = ceramic volume fraction of the A-side reactant and B-side mixture.

While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

The invention claimed is:

1. An impact absorbing foam comprising:

a polymeric foam; and ceramic particulates dispersed in the polymeric foam;

wherein the ceramic particulates have an average diameter in the range from about 1 to about 400 microns and a crushing strength in the range from about 100 to about 2,000,000 psi; and wherein the ceramic particulates are coated with one or more layers of sodium silicate, silica, alumina, alumina-silica, zirconia, titania, calcia, magnesia, or mixtures of two or more thereof.

2. The impact absorbing foam of claim 1 wherein the average distance between the ceramic particulates in the polymeric foam is in the range from about 100 to about 2000 microns.

3. The impact absorbing foam of claim 1 wherein the foam is capable of absorbing on impact at least about 20% of the energy resulting from such impact.

4. The impact absorbing foam of claim 1 wherein the foam has a Young's modulus in the range from about 0.3 to about 75 GPa.

5. The impact absorbing foam of claim 1 wherein the foam has a tensile strength in the range from about 0.001 to about 100 $MN/m^2$.

6. The impact absorbing foam of claim 1 wherein the polymeric foam comprises a continuous polymeric phase and a discontinuous phase comprising gas bubbles and/or void spaces dispersed in the polymeric phase.

7. The impact absorbing foam of claim 6 wherein the polymeric phase comprises a polymer, the polymer comprising polyurethane, polystyrene, polyvinyl chloride, polybutadiene, halogenated butyl rubber, styrene-butadiene rubber, polyacrylic rubber, butyl rubber, ethylene-propylene rubber, neoprene rubber, polysulfide elastomer, polysilicone, fluorocarbon rubber, polyhexafluoropropylene, polytetrafluoroethylene, polypropylene, polychlorotrifluoroethylene, polymethylvinyl ether, or a mixture of two or more thereof.

8. The impact absorbing foam of claim 6 wherein the gas bubbles and/or void spaces are derived from one or more blowing agents.

9. The impact absorbing foam of claim 6 wherein the foam comprises a polyurethane polymeric foam and the gas bubbles are derived from the reaction of water with an isocyante.

10. The impact absorbing foam of claim 6 wherein the gas bubbles comprise carbon dioxide.

11. The impact absorbing foam of claim 1 wherein the foam comprises gas bubbles and/or void spaces that provide the foam with a volumetric expansion in the range from about 50% to about 400%.

12. The impact absorbing foam of claim 1 wherein the ceramic particulates comprise aluminum, zirconium, silicon, magnesium, calcium, boron, silicon carbide, oxides thereof, or a mixture of two or more thereof.

13. The impact absorbing foam of claim 1 wherein the ceramic particulates comprise platelets, flakes, hollow spheres, solid spheres, hollow irregular shaped particulates, solid irregular shaped particulates, rods, cones, coated particulates, laminar particulates, laminated particulates, composite particulates, or a mixture of two or more thereof.

14. The impact absorbing foam of claim 1 wherein the ceramic particulates comprise hollow alumino-silicate spheres, silicon carbide flakes, natural mica flakes, chemically modified mica flakes, aluminum diboride flakes, boron nitride platelets, sodium silicate coated ceramic spheres, potassium ion modified mica flakes, alumina flakes, hollow alumina spheres, zirconia particulates, hollow zirconia spheres, sol gel or aerosol produced silica, or a mixture of two or more thereof.

15. The impact absorbing foam of claim 1 wherein the ceramic particulates comprise hollow particulates containing an inert gas.

16. The impact absorbing foam of claim 15 wherein the inert gas comprises nitrogen, argon and/or helium.

17. The impact absorbing foam of claim 1 wherein the polymeric foam comprises a polymeric phase derived from a polyurethane pre-polymer.

18. The impact absorbing foam of claim 17 wherein the polyurethane pre-polymer comprises a toluene diisocyanate and/or methylene diphenyl diisocyante terminated pre-polymer.

19. The impact absorbing foam of claim 17 wherein the polyurethane pre-polymer has an average molecular weight in the range from about 100 to about 125,000.

20. The impact absorbing foam of claim 17 wherein the polyurethane pre-polymer has an average functionality in the range from about 1 to about 10, and a density in the range from about 0.9 to about 1.3 g/cc.

21. The impact absorbing foam of claim 1 wherein the foam comprises a polymeric phase derived from a polyurethane, the polyurethane being derived from an isocyanate and a polyol.

22. The impact absorbing foam of claim 21 wherein the polyol has a molecular weight in the range from about 100 to about 125,000.

23. The impact absorbing foam of claim 21 wherein the polyol has a hydroxyl number in the range from about 10 to 200, an average functionality in the range from 1 to about 12, and a density in the range from about 0.9 to about 1.3 g/mol.

24. The impact absorbing foam of claim 1 where the polymeric foam comprises a polyurethane foam derived from a polyurethane pre-polymer, a plasticizer, a surfactant, one or more catalysts, an isocyanate, and water.

25. The impact absorbing foam of claim 1 wherein the polymeric foam is derived from a polyurethane pre-polymer; a mono-, di- and/or tri-alkyl phthalate and/or phosphate; a polysiloxane; and a catalyst comprising dibutyltin dilaureate, stannous octoate, and/or tetramethyl -1, 6, -hexadiamine.

26. The impact absorbing foam of claim 1 wherein the polymeric foam is derived from a polyurethane pre-polymer, the polyurethane pre-polymer being derived from a polyether polyol, and toluene diisocyanate and/or methylene diphenyl diisocyanate.

27. The impact absorbing foam of claim 25 wherein the polysiloxane comprises a polydimethylsiloxane.

28. The impact absorbing foam of claim 1 wherein the foam is in the form of a padding material, a component of a shoe, a prosthetic device, a component of a protective helmet, a padding to protect mechanical or electrical equipment, or a protective material for the interior of a vehicle.

29. The impact absorbing foam of claim 1 wherein the foam is in the form of an interior pad for a football helmet.

30. A method, comprising:

providing the foam of claim 1;

applying an impacting force against the foam; and crushing at least some of the ceramic particulates in the foam.

31. The method of claim 30 wherein the ceramic particulates comprise hollow particulates containing an inert gas, the impacting force applied against the foam generating heat within the foam and crushing at least some of the hollow particulates, the crushing of hollow particulates causing a release of inert gas within the foam, the release of inert gas within the foam reducing at least some of the heat generated within the foam by the impacting force applied against the foam.

32. The method of claim 31 wherein a heat sensor is used to equate the amount of heat released to the amount of the ceramic particulates crushed.

33. The method of claim 31 wherein a gas sensor is used to equate the amount of inert gas released to the amount of ceramic particulates crushed.

34. The method of claim 31 wherein an indicating device is used to measure the amount of ceramic particulates crushed.

35. The method of claim 34 wherein the indicating device comprises a radio frequency identification chip communicating with a sensor to monitor the force applied against the foam.

36. The method of claim 34 wherein the indicating device comprises a colorimetric indicator that changes color indicating the amount of ceramic particulates crushed.

* * * * *